(12) United States Patent
Meltzer et al.

(10) Patent No.: US 6,171,576 B1
(45) Date of Patent: Jan. 9, 2001

(54) DOPAMINE TRANSPORTER IMAGING AGENT

(75) Inventors: Peter C. Meltzer, Lexington; Bertha K. Madras, Newton; Alan Davison, West Roxbury; Paul Blundell, Somerville; Ashfaq Mahmood, Brookline; Alun G. Jones, Newton Centre, all of MA (US)

(73) Assignees: Organix Inc., Woburn; President & Fellows of Harvard College; Massachusetts Institute of Technology, both of Cambridge, all of MA (US)

( * ) Notice: Under 35 U.S.C. 154(b), the term of this patent shall be extended for 760 days.

(21) Appl. No.: 08/552,584

(22) Filed: Nov. 3, 1995

(51) Int. Cl.[7] .......................... A61K 51/00; A61M 36/14
(52) U.S. Cl. .................... 424/1.65; 534/14; 424/1.11; 424/9.1; 546/124; 546/132
(58) Field of Search ................... 424/1.65, 1.85, 424/1.11, 1.69, 9.1, 9.3, 9.4, 9.5; 534/10, 11–16; 506/569, 223, 570; 546/132, 1, 4, 5, 10, 124

(56) References Cited

U.S. PATENT DOCUMENTS

| | | | |
|---|---|---|---|
| 4,434,151 | 2/1984 | Byrne et al. | 424/1.1 |
| 4,673,562 | 6/1987 | Davison et al. | 424/1.1 |
| 4,746,505 | 5/1988 | Jones et al. | 424/1.1 |
| 5,122,361 | * 6/1992 | Kung et al. | 546/126 |
| 5,128,118 | 7/1992 | Carroll et al. | 424/1.1 |
| 5,310,912 | * 5/1994 | Neumeyer et al. | 546/132 |
| 5,334,728 | * 8/1994 | Kung et al. | 546/126 |
| 5,380,848 | 1/1995 | Kuhar et al. | 546/124 |
| 5,413,779 | * 5/1995 | Kuhar et al. | 424/1.85 |
| 5,426,189 | * 6/1995 | Kung et al. | 546/126 |
| 5,439,666 | * 8/1995 | Neumeyer et al. | 424/1.85 |
| 5,493,026 | * 2/1996 | Elmaleh et al. | 346/132 |
| 5,980,860 | * 11/1999 | Kung et al. | 424/1.65 |

FOREIGN PATENT DOCUMENTS

| | | |
|---|---|---|
| 0 135 160 | 3/1985 | (EP) . |
| WO 93/09814 | 5/1993 | (WO) . |
| WO 95/11901 | 5/1995 | (WO) . |
| WO 97/14445 | 4/1997 | (WO) . |

OTHER PUBLICATIONS

Clarke et al., Compounds Affecting the Central Nervous System. 43 3β–Phenyltropane–2–carboxylic Esters and Analogs, *Journal of Medicinal Chemistry*, 1973, vol. 16, No. 11, pp. 1260–1267.

Ohmomo et al., New Conformationally Restricted $^{99m}TcN_2S_2$ Complexes as Myocardial Perfusion Imaging Agents, *J. Med. Chem.*, 1992, 35, pp. 157–162.

Carroll et al., Cocaine and 3β–(4'–Substituted phenyl)tropane–2α–carboxylic Acid Ester and Amide Analogues. New High–Affinty and Selective Compounds for the Dopamine Transporter, *J. Med. Chem.*, 1995, 38, pp. 379–388.

T.N. Rao, et al., Monoamide Monoamine Dithiolate Ligands (MAMA) As Chelating Agents For Technetium: Kinetic And Mechanistic Studies Of Complex Formation, in Eighth International Symposium on Radiopharmaceutical Chemistry, 1990, pp. 39–40.

H. Spies, et al., Technetium And Rhenium Complexes As Potential Receptor Binding Ligands, Abstract in Eleventh International Symposium on Radiopharmaceutical Chemistry, 1995, pp. 319–320.

P. D. Mozley, et al., Abstract No. 123, in *the Journal of Nuclear Medicine*, IPT Spect Imaging in Healthy Volunteers: Evaluating Changes in the Dopamine Reuptake Transporter with Normal Aging, vol. 36, No. 5, May 1995, pp. 32P.

A.M. Myers, et al., Abstract No. 505, in *The Journal of Nuclear Medicine*, Metabolite Analysis of I–123 IPT: A New Dopamine Reuptake Site Imaging Agent, vol. 36, No. 5, May 1995, pp. 124P.

A.J. Kim, et al., Abstract No. 511, in *The Journal of Nuclear Medicine*, In Vivo Quantification of Presynaptic Dopamine Transporter Binding Parameters in Human Brains with [I–123]IPT Spect., vol. 36, No. 5, May 1995, pp. 125P.

A.J. Kim, et al., Abstract No. 808, in *The Journal of Nuclear Medicine*, Absolute Activity Measurements of In Vivo Monkey Brain using a Triple Headed Spect and a New Radioligand: [I–123]IPT., vol. 36, No. 5, May 1995, pp. 178P–179P.

P.D. Mozley, et al., Abstract No. 826, in *The Journal of Nuclear Medicine*, The Dosimetry of [I–123]IPT: A Cocaine Analog for Imaging the Dopamine Reuptake Transporter., vol. 36, No. 5, May 1995, pp. 183P.

Brandau, et al., *Nuc. Med. Biol.*, 21, No. 8, pp. 1073–1081.

Bryson, et al., *Inorg. Chem.* 1988, 27, pp. 2154–2161.

Davison, A., et al., *Inorg. Chem.* 1981, 20, pp. 1629–1632.

DiZio, J.P., et al., *Bioconj. Chem.* 1991, 2, pp. 353–366.

DiZio, J.P., et al., *J. Nucl. Med.* 1992, 33, No. 4, pp. 558–569.

(List continued on next page.)

*Primary Examiner*—Dameron Jones
(74) *Attorney, Agent, or Firm*—Dike, Bronstein, Roberts, & Cushman; George W. Neuner; Cara Z. Lowen

(57) ABSTRACT

Radiopharmaceutical compounds are disclosed. A tropane compound is linked through the N atom at the 8-position to a chelating ligand capable of complexing technetium or rhenium to produce a neutral labeled complex that selectively binds to the dopamine transporter. These compounds can be prepared as separate diastereoisomers as well as a mixture of diastereoisomers. Also disclosed are radiopharmaceutical kits for preparing the labeled radiopharmaceutical compounds.

30 Claims, 2 Drawing Sheets

OTHER PUBLICATIONS

Fritzberg et al., *J. Nucl. Med.* 1981, 22, pp. 258–263.
Fritzberg et al., *J. Nucl. Med.* 1982, 23, pp. 592–598.
Gustavson, L.M., et al., *Tet. Lett.* 1991, 32, pp. 5485–5488.
Hansen, et al., *J. Nucl. Med.* 1994, 35, pp. 1198–1205.
Jones, et al., *J. Nucl. Med.* 1982, 23, pp. 801–809.
Steignman, et al., *The Chemistry of Technetium in Medicine* 1992, pp.117–127.
Archer, et al., New Hydrophilic Ligands for $^{99m}$Tc–Based Radiopharmaceuticals, *Technetium and Rhenium in Chemistry and Nuclear Medicine* 4, eds. M. Nicolini, G. Bandoli, U. Mazzi, Servizi Grafici Editoriali, Padua, 1995, pp. 177–179.
Baldwin, et al., Synthesis and Biodistribution of $^{99m}$Tc Aromatic Amine–Amide–Thiol–Thioether $N_2S_2$ Complexes, *Technetium and Rhenium in Chemistry and Nuclear Medicine* 4, eds. M. Nicolini, G. Bandoli, U. Mazzi, Servizi Grafici Editoriali, Padua, 1995, pp. 329–332.
Kelly, et al., Low Lipophilicity Technetium–99m Complexes for Radiopharmaceutical Applications, *Technetium and Rhenium in Chemistry and Nuclear Medicine* 4, eds. M. Nicolini, G. Bandoli, U. Mazzi, Servizi Grafici Editoriali, Padua, 1995, pp. 259–263.
Kung, H.F., et al., New TcO(III) and ReO(III) $N_2S_2$ Complexes as Potential CNS 5–$HT_{1A}$ Receptor Imaging Agents, *Technetium and Rhenium in Chemistry and Nuclear Medicine* 4, eds. M. Nicolini, G. Bandoli, U. Mazzi, Servizi Grafici Editoriali, Padua, 1995, pp. 293–298.
Liu, et al., New $N_2S_2$ Diamidedithiol and $N_3S$ Triamidethiols as Bifunctional Chelating Agents for Labelling Small Peptides with Technetium–99m, *Technetium and Rhenium in Chemistry and Nuclear Medicine* 4, eds. M. Nicolini, G. Bandoli, U. Mazzi, Servizi Grafici Editoriali, Padua, 1995, pp. 383–393.

Mahmood, et al., Technetium and Rhenium Complexes of Amine Amide Dithiol Ligands: Ligand Synthesis and Metal Complexes, *Technetium and Rhenium in Chemistry and Nuclear Medicine* 4, eds. M. Nicolini, G. Bandoli, U. Mazzi, Servizi Grafici Editoriali, Padua, 1995, pp. 211–215.

Volkert, W.A., Ligand System Useful in Designing High Specific Activity $^{99m}$Tc or $^{186/188}$Re Radiopharmaceuticals, *Technetium and Rhenium in Chemistry and Nuclear Medicine* 4, eds. M. Nicolini, G. Bandoli, U. Mazzi, Servizi Grafici Editoriali, Padua, 1995, pp. 17–26.

Meegalla et al (Nov. 1995), J. Am. Chem. Soc., vol. 117, No. 44, pp. 11037–11038, "First Example of a 99m–Tc Complex as a Dopamine Transporter Imaging Agent".*

Meegalla et al (1996), Bioconjugate Chem., vol. 7, No. 4, pp. 421–429, "Tc–99m Labeled Tropanes as Dopamine Transporter Imaging Agents".*

Davies et al (1994). J. Med. Chem. vol. 37, pp. 1262–1268. "Synthesis of 2β–acyl–3β–aryl–8–azabicyclo[3.2.1]octanes and Their Binding Affinities at Dopamine and Serotonin Transport Sites in Rat Striatum and Frontal Cortex".*

Bennett et al (Mar. 1995). The Journal of Pharmacology and Experimental Therapeutics, vol. 272, No. 3, pp. 1176–1186. "Novel 2–Substituted Cocaine Analogs: Uptake and Ligand Binding Studies at Dopamine, Serotonin, and Norepinephrine Transport Sites in the Rat Brain".*

* cited by examiner

DOPAMINE TRANSPORTER IMAGING AGENT

STATEMENT OF GOVERNMENT SUPPORT

This invention is supported by NIH Grant Nos. CA34970, DA06303, DA09462, and NS50366 and the government has certain rights to the invention.

FIELD OF THE INVENTION

The present invention relates to coordination complexes comprising a radiolabeled ligand with high binding affinity and good selectivity for the dopamine transporter (DAT). Such agents can be useful for the early diagnosis and treatment of neurodegenerative disorders.

BACKGROUND OF THE INVENTION

The dopamine transporter (DAT) plays a critical role in physiological, pharmacological and pathological processes in brain. The transport system is a primary mechanism for terminating the effects of synaptic dopamine, thereby contributing to the maintenance of homeostasis in dopamine systems. It also appears to be a principal target of cocaine in the brain. (Kennedy and Hanbauer, *J. Neurochem.* 1983, 41, 172–178; Shoemaker et al., *Naunyn-Schmeideberg's Arch. Pharmacol.* 1985, 329, 227–235; Reith et al., *Biochem Pharmacol.* 1986, 35, 1123–1129; Ritz et al., *Science* 1987, 237, 1219–1223; Madras et al., *J. Pharmacol. Exp. Ther.* 1989a, 251, 131–141; Bergman et al., *J. Pharmacol. Exp. Ther.* 1989, 251, 150–155; Madras and Kaufman, *Synapse* 1994, 18, 261–275). Furthermore, the dopamine transporter may be a conduit for entry of neurotoxins into dopamine containing cells.

The striatum has the highest levels of dopamine terminals in the brain. A high density of DAT is localized on dopamine neurons in the striatum and appears to be a marker for a number of physiological and pathological states. For example, in Parkinson's disease, dopamine is severely reduced and the depletion of DAT in the striatum has been an indicator for Parkinson's disease (Schoemaker et al., *Naunyn-Schmeideberg's Arch. Pharmacol.* 1985, 329, 227–235; Kaufman and Madras, *Synapse* 1991, 9, 43–49). Consequently, early or presymptomatic diagnosis of Parkinson's disease can be achieved by the quantitative measurement of DAT depletion in the striatum. (Kaufman and Madras, *Synapse* 1991, 9, 43–49). Simple and noninvasive methods of monitoring the DAT are quite important. Depletion could be measured by a noninvasive means such as brain imaging using a scintillation camera system and a suitable imaging agent (Frost et al., *Ann. Neurology* 1993, 34, 423–431; Hantraye et al., *Neuroreport* 1992, 3, 265–268). Imaging of the dopamine transporter also would enable the monitoring of progression of the disease and of reversal of the disease such as with therapies consisting of implants of dopamine neurons or drugs that retard progression of the disease.

Other neuropsychiatric disorders, including Tourette's Syndrome and Lesch Nyhan Syndrome and possibly Rett's syndrome, are also marked by changes in DAT density. The DAT also is the target of the most widely used drug for attention deficit disorder, methylphenidate. The capacity to monitor the transporter in persons suffering from this disorder can have diagnostic and therapeutic implications. Furthermore, an age-related decline in dopamine neurons can be reflected by a decline in the dopamine transporter (Kaufman and Madras, *Brain Res.* 1993, 611, 322–328; van Dyck et al., *J. Nucl. Med.* 1995, 36, 1175–1181) and may provide a view on dopamine deficits that lie outside the realm of neuropsychiatric diseases.

The density of the DAT in the brains of substance abusers has also been shown to deviate from that in normal brain. For example, the density is elevated in post-mortem tissues of cocaine abusers (Little et al., *Brain Res.* 1993, 628, 17–25). On the other hand, the density of the DAT in chronic nonviolent alcohol abusers is decreased markedly. (Tiihonen et al., *Nature Medicine* 1995, 1, 654–657). Brain imaging of substance abusers can be useful for understanding the pathological processes of cocaine and alcohol abuse and monitoring restoration of normal brain function during treatment.

Accordingly, a radiopharmaceutical that binds to the DAT can provide important clinical information to assist in the diagnosis and treatment of these various disease states.

In order to be effective as an imaging agent for the disorders described above, it must have a specific binding affinity and selectivity for the transporter being targeted, e.g. DAT. Brain imaging agents must also have blood brain barrier (BBB) permeability. Yet, it has been difficult to produce a metal chelate which can cross the blood brain barrier while still retaining binding affinity and selectivity for its receptor site. Therefore, it is very desirable to find a suitable agent that satisfies these criteria and will complex with a desired radionuclide, such as $^{99m}$Tc.

In addition, to be an effective imaging agent, a specific target:nontarget ratio is necessary. In the case of an agent selective for DAT one must take into account the fact that the striatum, the region of the brain having the highest density of the dopamine transporter, also contains serotonin transporter (SET). The SET is normally present at one-tenth to one-fifteenth the concentration of the dopamine transporter. Imaging agents that bind very strongly to DAT sometimes also exhibit a degree of binding to SET. Although such a nontarget binding typically poses no serious problem in the imaging of normal brains due to the greater number of DAT compared to SET, under disease conditions in which DAT are selectively reduced (or in which SET may be selectively increased), binding to the SET may make it difficult to quantify DAT. Moreover, binding to SET in other brain regions such as the hypothalamus and thalamus can reduce striatal contrast and diminish accuracy in localizing and imaging the striatum. Therefore, the target to nontarget binding ratio of DAT:SET can be important. Presently, among the most effective compounds for viewing and quantifying the DAT are phenyltropane derivatives that are labelled with positron emitters, such as $^{11}$C and $^{18}$F, and gamma emitters, such as $^{123}$I.

The radionuclide, technetium-99m, $^{99m}$Tc ($T_{1/2}$ 6.9 h, 140 KeV gamma ray photon emission) is a preferred radionuclide for use in imaging because of its excellent physical decay properties and its chemistry. For example, its half-life of about 6 hours provides an excellent compromise between rate of decay and convenient time frame for an imaging study. Thus, it is much preferred to other radionuclides such as $^{123}$I, which has a substantially longer half life, or $^{18}$F, which has a substantially shorter half-life, and which are much more difficult to use. Its emission characteristics also make it easy to image. Further, it can be conveniently generated at the site of use. $^{99m}$Tc is currently the radionuclide of choice in diagnostic centers around the world. It would be desirable to have a coordination complex with technetium for imaging DAT. Such a complex could be used for detecting conditions in which the DAT is useful as a marker.

However, a number of difficulties arise in the use of technetium for radioimaging agents because of its chemistry. For example, $^{99m}$Tc must typically be bound by a chelating agent. Consequently it is much more difficult to design and prepare a $^{99}$mTc radioligand than it is to prepare a radioligand using other radionuclides such as $^{123}$I, which can be attached covalently to the ligand. The size of the chelating agent for technetium also can create problems when using this radionuclide in imaging agents. This can be an especially difficult problem when attempting to design receptor-based imaging agents using Tc.

To date, no $^{99}$mTc labeled compounds have been developed that are useful for labeling the dopamine transporter or to mark any aspect of the dopamine system. Attempted receptor based ligands labeled with technetium, such as a quinuclidinyl benzylate Tc complex (Lever et al., *Nucl. Med. Biol.* 1994, 21, 157–164) as a potential muscarinic cholinergic receptor marker, and a benzovesamicol Tc complex as a potential marker for cholinergic neurons (Del Rosario et al., *Nucl. Med. Biol.* 1994, 21, 197–203), have not been useful imaging agents due to lack of uptake in the brain.

Imaging agents being tested to determine their ability as diagnostic tools for neurodegenerative diseases typically are 123I labeled radioiodinated molecules. See, for example, RTI-55 (Boja, J. W., et al., *Eur. J. Pharmacol.* 1991, 194, 133–134; Kaufman and Madras, *Synapse,* 1992, 12, 99–111) or β-CIT (Neumeyer, J. L., et al., *Med. Chem.* 1991, 34, 3144–3146) and an iodoallyltropane, altropane (Elmaleh, D. R., et al., U.S. patent application Ser. No. 08/142,584).

Although the tropane family of compounds are known to bind to the dopamine transporter, the addition of bulky chelating ligands for binding technetium or rhenium would be expected to affect potency and ability to cross the blood brain barrier of the resulting labeled complex. Kung, et al., in *Technetium and Rhenium in Chemistry and Nuclear Medicine* 4, eds. M. Nicolini, G. Bandoli, U. Mazzi, Servizi Grafici Editoriali, Padua, 1995, report that a $^{99}$Tc-labelled $N_2S_2$ ligand complexed with an arylpiperazine known to have selective binding to serotoninlA had only moderate binding affinity in vitro and failed to penetrate the intact blood-brain barrier.

It would be desirable to have a technetium or rhenium radio-labelled DAT imaging agent which is capable of crossing the blood brain barrier and has a binding affinity and selectivity for the DAT.

SUMMARY OF THE INVENTION

The present invention provides radiopharmaceutical compounds that form coordination complexes with a technetium or rhenium radionuclide and that selectively bind to neural transporters, thereby providing novel radio labeled agents. Preferred such agents include radioimaging agents which are capable of crossing the blood brain barrier to image DAT in the brain.

The compounds of the present invention comprise a tropane compound linked through the N atom at the 8-position to a chelating ligand capable of complexing a technetium or rhenium radionuclide to produce a neutral labeled complex that selectively binds to the dopamine transporter. These compounds can be prepared as separate diastereoisomers as well as a mixture of diastereoisomers.

Tropane compounds useful in the practice of the present invention bind to the dopamine transporter. Preferred radiopharmaceutical compounds of the invention can be represented by the following structural formula:

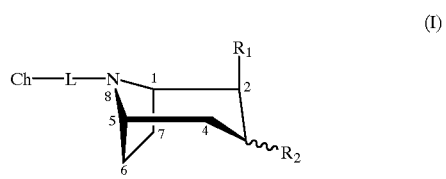

wherein $R_1$ is selected from $COOR^a$, $COR^a$, $CONHR^a$, $CONR^aR^b$, $CH_2CH_3$, $(CH_2)_nCH_3$, $CHCHR^c$, $(CH_2)_nCCR^c$ or an ester bioisostere, e.g., $C_3HNOR^c$ (oxazole) or $C_2N_2OR^c$ (oxadiazole);

$R_2$ is selected from $C_6H_4X$, $C_6H_3X_2$, $C_{10}H_6X$, or $C_{12}H_8WYCHO$ (diarylmethoxy);

$R^a$ and $R^b$ are each selected from $CH_3$, $CH_2CH_3$, $CH_2CH_2CH_3$, $(CH_2)_nCH_3$, $CH(CH_3)_2$, $C(CH_3)_3$, $(CH_2)_nC_6H_5$, $C_6H_5$, $C_6H_4X$, $C_{10}H_7$, or $C_{10}H_6X$;

$R^c$ is selected from $COOR^a$, $CH_3$, $(CH_2)_nCH_3$, $C_6H_5$, $C_6H_4X$,

X is selected from H, Br, Cl, I, F, OH, $OCH_3$, $CF_3$, $NO_2$, $NH_2$, CN, OR, $NHCOCH_3$, $N(CH_3)_2$, $CH_2CH_3$, $CHOCH_3$, $C(CH_3)_3$;

W and Y are each selected from H, Br, Cl, I, F, OH, $OCH_3$, $CF_3$, $NO_2$, $NH_2$, CN, OR, $NHCOCH_3$, $N(CH_3)_2$;

n is an integer 0–6;

L is a linking moiety comprising a chain of atoms containing 2 to about 6 carbon atoms in the backbone of the chain or, if a ring is part of the chain, 1 to about 4 carbon atoms in the backbone of the chain in addition to the ring carbons; and Ch is a tridentate or tetradentate chelating ligand that forms a neutral complex with technetium or rhenium. $R_1$ and $R_2$ are in the α or β configuration. $R_1$ can be at the $C_2$ or $C_4$ when the tropane has a 1R or 1S configuration respectively. For 3-diarylmethoxy tropanes, when W≠Y, the methine of the diarylmethoxy can have S or R configuration.

The imaging agents of the present invention are useful for detecting tropane recognition sites including neuronal transporters such as the dopamine transporter. For purposes of the present invention, a tropane recognition site is any receptor or transporter site that binds to the tropane compound. Thus, the compounds of this invention can be used as diagnostic agents, prognostic agents and therapeutic agents for neurodegenerative diseases.

The present invention also provides a method of using the coordination complex as an imaging agent for detecting neurodegenerative and neuropsychiatric disorders characterized by a change in density of DAT or dopamine neurons. For example, a method for detecting the change in DAT resulting from a neurodegenerative disease, such as Parkinson's disease, comprises injecting a labeled compound of the present invention in a dose effective amount for detecting DAT in the particular mammal and obtaining images of the labeled compound bound to DAT. Rhenium labeled compounds can also be useful for therapeutic treatments.

The present invention also provides kits for producing the compounds of the present invention labeled with technetium or rhenium. The kits typically comprise a sterile, non-pyrogenic container containing lyophilized compound and a reducing agent to form a complex of the compound with technetium or rhenium. The kits permit ready reconstitution and labeling with aqueous solutions containing the radionuclide, e.g. pertechnetate, preferably having a pH in the range of about 5 to about 8.

DETAILED DESCRIPTION OF THE INVENTION

Figure 1:
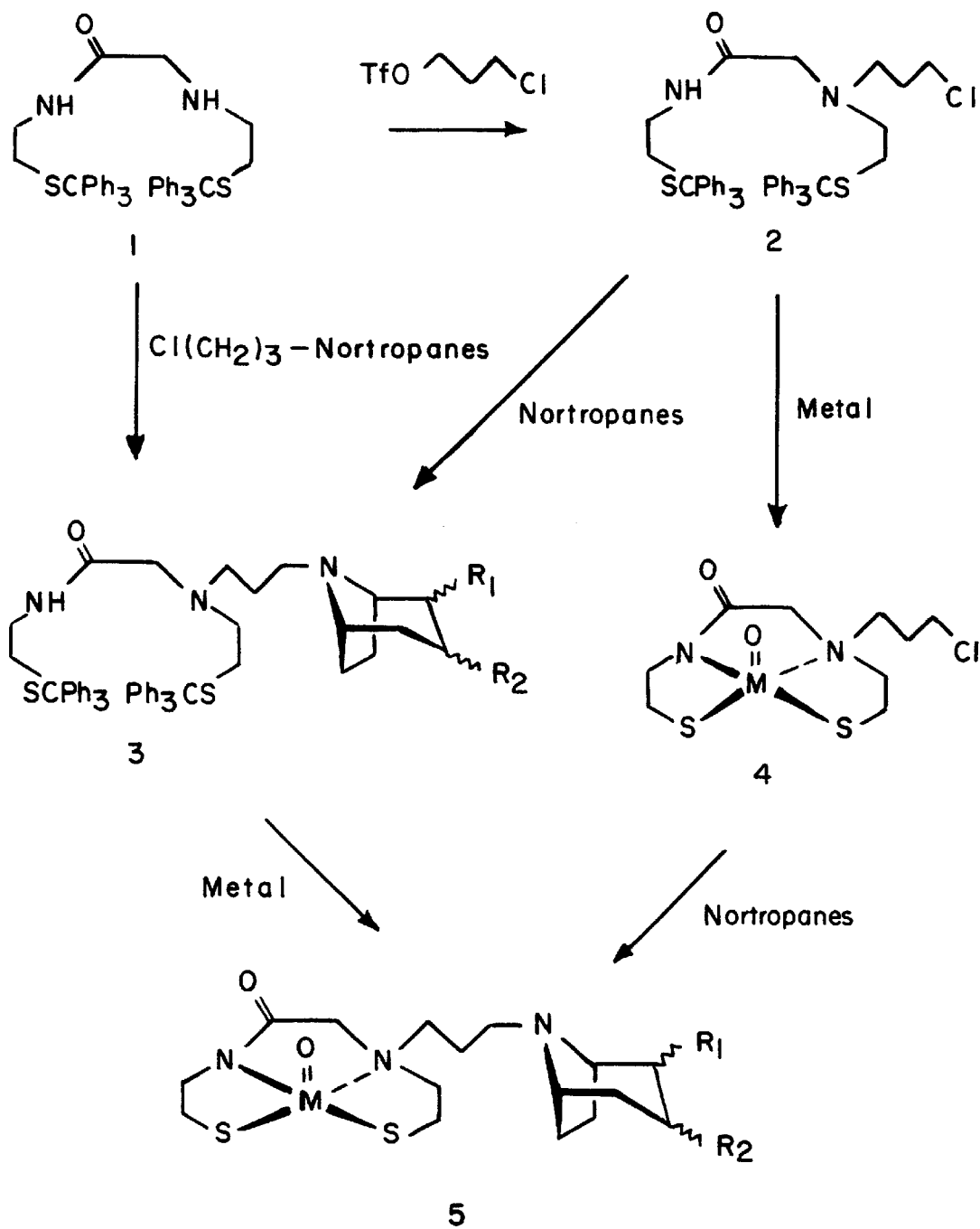
FIG. 1 is an illustration of alternative general schemes for preparation of the radiopharmaceutical compounds of the present invention where the metal ("M") is a radionuclide such as rhenium or technetium.

The compounds of the present invention comprise a tropane compound or ligand that selectively binds to tropane recognition sites, e.g., neuron transporters such as the DAT. The tropane ligand is radiolabeled with a radioactive technetium or rhenium by a chelating ligand which is attached to the tropane ligand by a linker. The unlabeled compounds of this invention are schematically represented by the formula Ch—L—Tr, wherein Ch is the chelating ligand, L is the linker and Tr is the tropane ligand.

Tropane compounds or ligands useful in the practice of the present invention can generally be represented by formula II where $R_1$ and $R_2$ are defined as above:

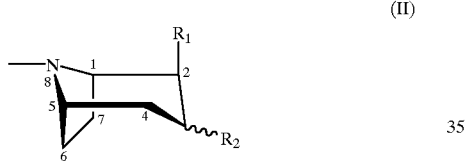

(II)

Any tropane compound of the general formula II is useful in the present invention so long as it binds to DAT. Examples of particularly useful tropanes are: 2-carbomethoxy-3-(4-fluorophenyl)-N-methyltropane ("WIN 35,428") (Clarke, R. L., et al., *J. Med. Chem.* 1973, 16, 1260–1267) which binds potently ($IC_{50}$=11.0 nM) and with specificity to the DAT (Meltzer, P. C., et al., *J. Med. Chem.* 1993, 36, 855–862); 2-carbomethoxy-3-(3,4-dichlorophenyl)-N-methyltropane ("O-401"; $IC_{50}$=1.09nM) (Meltzer, P. C., et al., *J. Med. Chem.* 1993, 36, 855–862); and (S)-(+)-2-carbomethoxy-3α-{bis(4-fluorophenyl)methoxy}tropane ("difluoropine") (Meltzer, P. C., et al., *J. Med. Chem.* 1994, 37, 2001–2010). Difluoropine has a diphenylmethoxy moiety attached at C-3 of the tropane. Difluoropine and its nortropane analog, which have a 3c-diphenylmethoxy group, are of the S-configuration. Other tropanes, such as those having a 3β-oriented aryl group (see WIN 35,428), are of the R-configuration.

The chelating ligand useful in the practice of the present invention comprises any tridentate or tetradentate ligand that binds technetium or rhenium to form a neutral complex. The chelating ligand is covalently attached to the linker L, as described below. Preferred chelating ligands contain a plurality of N or S atoms for complexing with the radionuclide. Examples of suitable ligands are the $N_2S_2$ compounds represented by the following structural formulas III, IV, V, VI and VII:

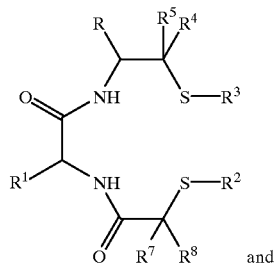

(III)

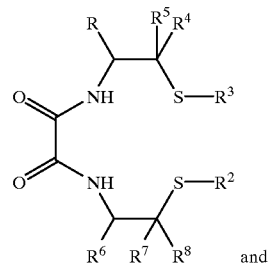

(IV)

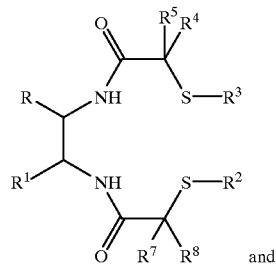

(V)

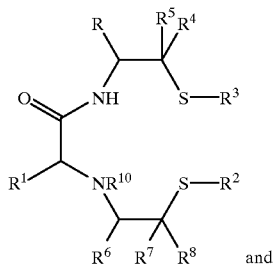

(VI)

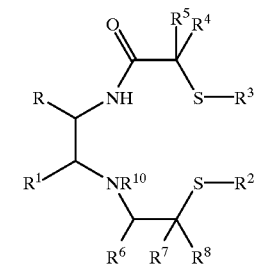

(VII)

wherein R, $R^6$, and $R^{10}$ are each selected from hydrogen, substituted or unsubstituted lower alkyl, alkyl$R^9$, or —$COR^9$ where $R^9$ is selected from hydroxy, substituted lower alkoxy, substituted or unsubstituted amino, glycine ester, halide (chloro, bromo, iodo) or OR (OR is a leaving group such as mesylate, triflate, or tosylate) or an activated leaving group; $R^1$ is selected from hydrogen, or substituted or unsubstituted lower alkyl; $R^2$ and $R^3$ are each selected from hydrogen or a thiol protecting group, or an inter or intramolecular disulfide; and $R^4$, $R^5$, $R^7$ and $R^8$ are each selected from hydrogen or lower alkyl.

When R, $R^6$ or $R^{10}$ is a carboxylic acid derivative, $R^9$ can be an activated leaving group. For purposes of this invention the leaving group $R^9$ is defined such that (compound) —$COR^9$ is an acylating agent. Examples of activated leaving groups suitable for the practice of this invention include, for example: halide; substituted or unsubstituted aryloxy groups such as phenoxy, pentachlorophenoxy, etc,; oxyheterocyclic groups such as N-oxy-succinimido, etc.; mercapto; lower alkylthio; arylthio; oxyphosphonium; and other groups known to those skilled in the art to be useful as leaving groups.

$R^2$ and $R^3$ can be hydrogen or any known thiol protecting group. Examples of such groups include lower alkylaminocarbonyl such as ethylaminocarbonyl, lower alkanoylaminomethyl, aroylaminomethyl, t-butyl, acetamidomethyl, arylmethyl such as triphenylmethyl (trityl) and diphenylmethyl, aroyl such as benzoyl, aryloxycarbonyl such as phenoxycarbonyl, arylloweralkoxycarbonyl, preferably arylmethoxycarbonyl, benzyloxycarbonyl, and lower alkoxycarbonyl such as t-butoxycarbonyl. Preferred thiol protecting groups include trityl, t-butyl, diphenylmethyl, acetamidomethyl and benzoyl and an inter or intramolecular disulfide.

The term "lower alkyl" when used herein designates aliphatic saturated branched or straight chain hydrocarbon monovalent substituents containing from 1 to 6 carbon atoms such as methyl, ethyl, isopropyl, n-propyl, n-butyl, etc., more preferably 1 to 4 carbons. The term "lower alkoxy" designates lower alkoxy substituents containing from 1 to 6 carbon atoms such as methoxy, ethoxy, isopropoxy, etc., more preferably 1 to 4 carbon atoms.

The terms substituted lower alkyl or substituted lower alkoxy when used herein include alkyl and alkoxy groups substituted with halide, hydroxy, carboxylic acid, or carboxamide groups, etc. such as, for example, —$CH_2OH$, —$CH_2CH_2COOH$, —$CH_2CONH_2$, —$OCH_2CH_2OH$, —$OCH_2COOH$, —$OCH_2CH_2CONH_2$, etc.

The term substituted amino when used herein includes such groups mono or di and tri-substituted with lower alkyl, and —$NH_3^+$ or mono, di and tri-substituted ammonium groups substituted with lower alkyl with a pharmacologically suitable anion.

The term glycine ester as used herein means the lower alkyl esters of glycine, preferably the methyl and ethyl esters.

These chelating ligands can be complexed with a radionuclide, e.g., technetium, to form the following complexes:

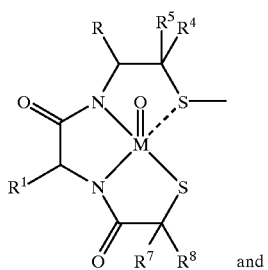

(VIII)

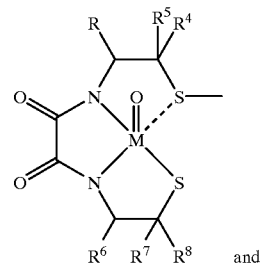

(IX)

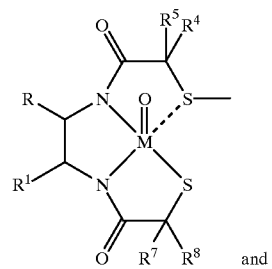

(X)

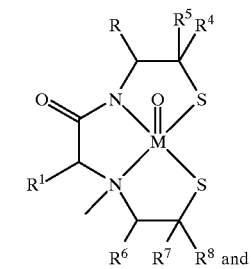

(XI)

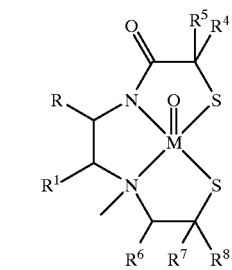

(XII)

where the R groups are defined as above.

Preferred chelating ligands are those formed from monoaminomonoamide compounds having structures of formula V, VI or VII, e.g., N-{2-((2-((triphenylmethyl)thio)-ethyl)amino)acetyl}-S-(triphenylmethyl)-2-aminoethanethiol Any organic linker having a backbone chain length of 2 to about 6 carbon atoms can be used to attach the chelating ligand, typically through its nitrogen, sulfur, R, $R^1$ or $R^6$, to the 8-nitrogen atom of the tropane ligand (which binds the dopamine transporter). Examples of linkers include $(CH_2)_m$, $CH_2(CH_2)_mCH_2$, $(CH_2)_mC_6H_4(CH_2)_p$, $CH_2(CHCH)CH_2$, $CH_2CCCH_2$, $(CH_2)_mNHR(CH_2)$, $(CH_2)_mO(CH_2)$ $(CH_2)_mS$ $(CH_2)$, $CH_2$ $CONH$ $(CH_2)_m$, $(CH_2)_mCONH$ $(CH_2)_p$, and $(CH_2)_mCOO(CH_2)_p$, where m=0–5, p=0–5, and (m+p)=1–5. A benzene ring in the back bone chain is equivalent to 2 carbon atoms.

Preferred radiolabeled compounds of the present invention cross the blood brain barrier and exhibit desired target:non-target specificity, i.e., the selectivity ratio of binding (DAT:SET) is about 10 or more. Thus, they are useful as brain imaging agents, for example, for imaging DAT.

The tropane ligands can be linked to the chelating ligand by an initial conversion to nortropanes. Syntheses of nortropanes are known in the art, for example, as disclosed in Meltzer, P. C., et al., *J. Med. Chem.* 1993, 36, 855–862; Meltzer, P. C., et al., *J. Med. Chem.* 1994, 37, 2001–2010 (the disclosure of which is incorporated herein by reference). Tropanes can be synthesized from tropinone or cocaine by techniques known in the art. Synthesis of the nortropanes can then be achieved by N-demethylation of the tropane, which can be readily accomplished by various methods known in the art, e.g., with α-chloroethyl chloro formate (ACE-Cl).

The chelating ligand is preferably prepared separately and, then, either attached to the nortropane and metallated, or metallated first followed by attachment to the appropriate nortropane. When the radiolabeled compounds of the invention are required to cross the blood brain barrier, the chelating ligands useful in the present invention form neutral complexes with the radionuclide and are lipid soluble. Chelating ligands that form neutral $^{99m}$Tc(V) complexes which are useful in the present invention include a substituted oxime (Loberg, M. D., et al., *J. Nucl. Med.* 1979, 20, 1181–1188), $N_2S_2$ compounds (Davison, A., et al., *Inorg. Chem.* 1981, 20, 1629–1632; Davison, A., et al., *J. Nucl. Med.* 1979, 20, 641 (abstr)), bisaminoethanethiol ("BAT") (Kung, H. F., et al., *J. Med. Chem.* 1985, 28, 1280–1284; Kung, H. F., et al., *J. Nucl. Med.* 1986, 27, 1051; Kung, H. F., et al., *J. Med. Chem.* 1989, 32, 433–437; Kung, H. F., et al., *J. Nucl. Med.* 1984, 25, 326–332; Francesconi, L. C., et al., *Inorg. Chem.* 1993, 32, 3114–3124), and diaminodithiol ("DADT") (Lever, S. Z., et al., *J. Nucl. Med.* 1985, 26, 1287–1294). Additional examples of useful chelating ligands include N,N'-bis(2-mercapto-1-methyl)-2-aminobenzylamine ("U-BAT") (Francesconi, L. C., et al., *J. Med. Chem.* 1994, 37, 3282–3288), propylene amine oximes ("HMPAO"), diamidodithiol ("DADS") (Rao, T. N., et al., *J. Am. Chem. Soc.* 1990, 112, 5798–5804; Stepniak-Biniakiewicz, D., et al., *J. Med. Chem.* 1992, 35, 274–279), phenylenediamine-thiol-thioether ("PhAT") (McBride, B. J., et al., *J. Med. Chem.* 1993, 36, 81–86), bis(mercaptoethyl)-2-aminoethylamine ("SNS") or bis(mercaptoethyl)-2-thioethylamine (Mastrostamatis, S. G., et al., *J. Med. Chem.* 1994, 37, 3212–3218), monoamine amide ("MAMA") (Gustavson, L. M., et al., *Tet. Lett.* 1991, 32, 5485–5488) and N-{2-((2-((triphenylmethyl)thio)ethyl)amino)acetyl}-S-(triphenylmethyl)-2-aminoethanethiol ("MAMA'") (O'Neil, J. P., et al., *Inorg. Chem.* 1994, 33, 319–323). For example, when MAMA' is attached to a lipophilic tropane by a linker in accord with the present invention, a neutral, moderately lipophilic and aqueous stable compound suitable for radiolabeling is formed.

Compounds of formula III and IV can be synthesized according to the methods described in U.S. Pat. No. 4,673,562 which is incorporated herein by reference. Compounds of formula V can be synthesized by methods known in the art (see Fritzberg et al., *J. Nucl. Med.* 1981, 22, 258–263). Compounds of formula VI can also be synthesized by methods known in the art. (See O'Neil, J. P., et al., *Inorg. Chem.* 1994, 33, 319–323).

Radiolabeled complexes of the present invention can be prepared via three general preparation procedures as outlined in the General Scheme (FIG. 1). The general preparation scheme exemplifies the use of trityl protecting groups for the sulfhydryls, however, other protecting groups that are known to be useful for sulfhydryl protection can also be used such as, for example, lower alkylaminocarbonyl such as ethylaminocarbonyl, lower alkanoylaminomethyl, arylaminomethyl, t-butyl, acetamidomethyl, arylmethyl such as triphenylmethyl(trityl) and diphenylmethyl, aryl such as benzoyl, aryloxycarbonyl such as phenoxycarbonyl, aryl loweralkoxycarbonyl, preferably arylmethoxycarbonyl such as benzyloxycarbonyl, and lower alkoxycarbonyl such as t-butoxycarbonyl. Preferred sulfhydryl protecting groups include trityl, t-butyl, diphenylmethyl, acetamidomethyl, disulfide and benzoyl.

The compounds of the invention can be prepared by known means based upon the present disclosure. For example, starting with an appropriate chelating ligand, such as an $N_2S_2$ compound, illustrated in the general scheme in FIG. 1 as N-{2-((2-((triphenylmethyl)thio)ethyl)amino)acetyl}-S-(triphenylmethyl)-2-aminoethanethiol, 1, (MAMA': Katzenellenbogen et al., *Inorg. Chem.*, 1994, 33, 319), the $N_2S_2$ compound can be alkylated with either the haloalkyl triflate or the haloalkylnortropane (prepared from the nortropane: Meltzer et al., *J. Med. Chem.*, 1993, 36, 855), producing the chloroalkyl (propyl shown) MAMA', 2, or the tropanalkyl (propyl shown) MAMA', 3, compounds, respectively. The chloroalkyl (propyl shown) MAMA' compound, 2, can then be attached to a suitable nortropane to provide the tropanalkyl (propyl shown) MAMA' compounds, 3, shown. Alternatively, the chloroalkyl (propyl shown) MAMA', 2, can be treated to incorporate a metal atom, preferably a radionuclide (such as $^{99}$Tc, $^{99m}$Tc, $^{188}$Re or $^{186}$Re) to provide complex 4. The resulting complex 4 can then be attached to a suitable nortropane to provide radiopharmaceutical compounds of the present invention, 5, as shown.

Alternatively, the tropanalkyl (propyl shown) MAMA' compounds, 3, can be treated to incorporate a radionuclide (such as $^{99}$Tc, $^{99m}$Tc, 188Re or $^{186}$Re) to form radiopharmaceutical compounds of the present invention, 5, as shown.

The compounds of the present invention can be either diastereoisomer as well as a mixture of both diastereomers. The diastereoisomers can be separated by column chromatography.

More specifically, alkylation of the $N_2S_2$, 1, with haloalkyl triflate to produce the chloroalkyl (propyl shown) MAMA', 2, can be used to prepare the linker which is used to bind the chelating ligand to the tropane ligand, which selectively binds the dopamine transporter. This alkylation step can be modified by those of ordinary skill in organic chemistry to create various linkers having a backbone chain length of 2 to about 6 carbon atoms, such as $(CH_2)_m$, $CH_2(CH_2)_mCH_2$, $(CH_2)_mC_6H_4(CH_2)_p$, $CH_2(CHCH)CH_2$, $CH_2CCCH_2$, $(CH_2)_mNHR(CH_2)$, $(CH_2)_mO(CH_2)$, $(CH_2)_mS(CH_2)$, $CH_2CONH(CH_2)_m$, $(CH_2)_mCONH(CH_2)_p$, and $(CH_2)_mCOO(CH_2)_p$, where m=0–5, p=0–5, and (m+p)=1–5.

Deprotection of the chloroalkyl compound 2 can be accomplished by standard methods well known in the art, e.g., with $H_2S/Hg(OAc)_2$ (O'Neil, J. P., et al., *Inorg. Chem.* 1994, 33, 319–323) or $AgNO_3$/Py (DiZio, J. P., et al., *Bioconj. Chem.* 1991, 2, 353–366), with TFA and phenol, or HBr in acetic acid (Zervas, L., et al., *J. Amer. Chem. Soc.* 1962, 84, 3887–3897) to result in the unprotected bisthiol which can then be immediately treated with a solution of tin (II) chloride ($SnCl_2$) and sodium perrhenate ($Na_2ReO_7$) or an agent such as $Na(^{99m}TcO_4)$/stannous tartrate (Francesconi, L. C., et al., *Inorg. Chem.* 1993, 32, 3114–3124; Canney, D. J., et al., *J. Med. Chem.* 1993, 36, 1032–1040) to produce the complexes 4. Purification of these chelates can be accomplished by flash chromatography as described by O'Neil (O'Neil, J. P., et al., *Inorg. Chem.*

1994, 33, 319–323). The chloroalkyl chelate, 4, can then be reacted (O'Neil, J. P., et al., *Bioconj. Chem.* 1994, 5, 182–193) with the appropriate nortropane to provide the coordination complexes of the present invention 5. Alkylation of nortropanes can be accomplished by methods known in the art, e.g., acetonitrile ($CH_3CN$), potassium iodide (KI) and potassium carbonate ($K_2CO_3$). The use of strong base can cause epimerization of the carbomethoxy group at C-2, although sodium carbonate in a solvent such as dimethyl formamide (DMF) can yield alkylated products in reasonable yield.

These compounds can be prepared either as free bases or as a pharmacologically active salt thereof such as hydrochloride, tartrate, sulfate, naphthalene-1,5-disulfonate or the like.

The technetium or rhenium radionuclide complexes of this invention can be formed by reacting compounds 2 or 3 with either pertechnetate or perrhenate in the presence of a suitable reducing agent in a conventional manner. For example, the compound can be dissolved in a suitable solvent with a reducing agent and then pertechnetate added. The mixture is then heated for a suitable length of time to complete the reaction. Typically, heating in a boiling water bath for about 10 minutes has been found sufficient to obtain very good yields of the radionuclide complex. To form rhenium complexes, $(Ph_3P)_2ReOCl_3$ is added in the presence of basic (NaOAc) methanol. Examples of reducing agents useful in the practice of this invention include stannous salts such as stannous chloride, sodium dithionite, and ferrous salts such as ferrous sulfate.

Rhenium behaves similarly to Tc. Thus, $N2S_2$ complexes of Rh or Tc are equally stable. Both metals form square pyramidal complexes with $N_2S_2$ ligands. (Francesconi, L. C., et al., *Inorg. Chem.* 1993, 32, 3114–3124). Rhenium is a preferred metal for use in studies which do not require the presence of a short half life radiolabel. For complexes with both technetium and rhenium, the oxygen occupies an apical position, therefore both syn and anti-isomers of the metal complexes are possible. The biological activity and log P values of Tc and Re chelates are generally similar. (O'Neil, J. P., et al., *Bioconjugate Chem.* 1994, 5, 182–193). $^{99m}Tc$ is a preferred radionuclide for use as an imaging agent. Rhenium is an excellent model for $^{99m}Tc$ and is also useful as a therapeutic agent.

The compounds of this invention are typically enantiomerically pure tropanes (either 1S or 1R configuration) attached by an achiral linker to a chiral chelating ligand. The chiral chelating ligand can be cis or trans with respect to the metal oxo and the linker, but is preferably cis. Each of the cis and trans chelating ligands exist as a pair of two enantiomers. By virtue of the chiral ligand which can exist in each of two enantiomeric forms, and a chiral tropane, each of the whole molecules exists as diastereoisomers. Radiopharmaceutical compositions of the present invention include the separate diastereoisomers of each, as well as mixtures of diastereomeric pairs. Examples of such tropane ligands are N-2-((3'-N'-propyl-(1"R-3"β-(4-fluorophenyl)tropane-2"β-carboxylic acid methyl ester))((2-((triphenylmethyl)thio)ethyl)amino)acetyl)-S-(triphenylmethyl)-2-aminoethanethiol, N-2-((3'-N'-propyl-(1"R-3"β-(3,4-dichlorophenyl)tropane-2"β-carboxylic acid methyl ester))((2-((triphenylmethyl)thio)ethyl)amino)acetyl)-S-(triphenylmethyl)-2-aminoethanethiol, and N-2-((3'-N'-propyl-(1"S-3"α-((bis(4-fluorophenyl)methoxyl)tropane-2"β-carboxylic acid methyl ester))((2 -((triphenylmethyl)thio)ethyl)amino)acetyl)-S-(triphenylmethyl)-2-aminoethanethiol.

The compounds of the present invention preferably have a target:nontarget ratio, such as a DAT:SET selectivity ratio of greater than 1, and preferably at least 10, to minimize binding of trace levels of the drug to the nontarget, e.g., serotonin transporter.

The present invention also provides pharmaceutical kits, preferably comprising the compounds of formula I with a reducing agent in lyophilized form in a pyrogen-free, sterilized container or vial. In this form the lyophilized composition can be readily reconstituted by adding only water, saline, or a buffer preferably having a pH in the range of 5 to 8, more preferably physiological pH. If technetium is the metal to be used as the radionuclide, pertechnetate solution from a technetium generator can be used for reconstitution.

In general, the radiopharmaceutical preparation kit comprises a sterilized unit dose (or multidose) vial containing the purified compound of formula I and a reducing agent for technetium, preferably lyophilized. Each dose should consist of a sufficient amount of compound and reducing agent to prepare the required dose for imaging, normally about 5 to about 30 mCi of $^{99m}Tc$ depending upon body weight of the mammal to be imaged. In use, the technetium, preferably as $^{99m}Tc$-pertechnetate in saline, is injected aseptically into the vial and the mixture reacted for a sufficient time to form the labeled complex. After reaction, typically, the resulting radiopharmaceutical is ready for use.

To image a desired target, a radiopharmaceutical preparation in accord with this invention having an effective dose of radioactivity for the particular mammal is prepared in a suitable pharmacological carrier, such as normal saline. Preferably, the radiopharmaceutical preparation is injected intravenously into the mammal. The target, e.g., the brain, is then imaged by positioning the mammal under a gamma camera or other suitable device.

In order to obtain high quality images, the radiochemical yield of bound technetium in the desired radiopharmaceutical should preferably be greater than 70% after reconstituting the lyophilized mixture and labelling. Lower yields may result in poorer image quality and undesirable purification steps may be required to produce high quality images.

This invention will be illustrated further by the following examples. These examples are not intended to limit the scope of the claimed invention in any manner.

The final compounds were characterized and their purity analyzed prior to biological evaluation. High field nuclear magnetic resonance (NMR) spectra were measured as well as low and high resolution mass spectra (MS) and infrared spectra (IR). Elemental analyses, thin layer chromatography (TLC) and/or high performance liquid chromatography (HPLC) were used as a measure of purity. A purity of >98% was obtained before biological evaluation of these compounds was undertaken.

In the following examples, NMR spectra were recorded on a Bruker 100 NMR spectrometer. Tetramethylsilane (TMS) was used as internal standard. Melting points are uncorrected and were measured on a Gallenkamp melting point apparatus. Thin layer chromatography (TLC) was carried out on Baker Si 250F plates. Visualization was accomplished with either iodine vapor, UW exposure or treatment with phosphomolybdic acid (PMA). Preparative TLC was carried out on Analtech uniplates Silica Gel GF 2000 microns. Flash chromatography was carried out on Baker Silica Gel 40 mM. Elemental Analyses were performed by Atlantic Microlab, Atlanta, Ga.

EXAMPLE 1

N-{2-((3'-chloropropyl)(2((triphenylmethyl)thio) ethyl)amino)acetyl}-S-(triphenylmethyl)-2-aminoethanethiol (Compound 2—FIG. 1)

The amine N-{2-((2-((triphenylmethyl)thio)ethyl)amino) acetyl}-S-(triphenylmethyl)-2-aminoethanethiol, 1 (FIG. 1), (10.86 g, 16 mmol) (Katzenellenbogen et al., *Inorg. Chem.* 1994, 33, 319) was dissolved in dry methylene chloride (10 mL) and to this solution was added 3-chloropropyltriflate (1.81 g, 8 mmol, prepared from 3-chloropropanol). The resulting solution was stirred at room temperature for 2 h at which point a further 90 mL of methylene chloride was added. The solution was filtered to remove excess amine triflate salt and the filtrate was chromatographed ($SiO_2$, ethyl acetate:hexanes 1:1). The desired product (4.36 g; 72% based on the triflate) was isolated as a white foam; mp 55–56° C.; IR (KBr Disc) $cm^{-1}$ 1640; $^1H$ NMR ($CDCl_3$) 1.6–1.9 (m, 2H), 2.2–2.55 (m, 8H), 2.85 (s, 2H), 3.02 (q, 6 Hz, 2H), 3.45 (t, 6 Hz, 2H), 7.1–7.5 (m, 30H); HRCIMS calculated for $C_{47}H_{48}ClN_2S_2O$ $[MH]^+$ 755.2896, found 755.2899.

EXAMPLE 2

N-{2-(3'-N'-propyl-(1"R-3"β-(4-fluorophenyl)tropane-2"β-carboxylic acid methyl ester))((2-(((triphenylmethyl)thio)ethyl)amino)-acetyl}-S-(triphenylmethyl)-2-aminoethanethiol (Compound 3—FIG. 1)

Route A

To a solution of nor-3β-(4-fluorophenyl)tropane-2β-carboxylic acid methyl ester (52.6 mg, 0.2 mmole) in dry acetonitrile (10 mL) was added in succession N-{2-((3-chloropropyl)(2-((triphenylmethyl)thio)ethyl)amino) acetyl}-S-(triphenylmethyl)-2-aminoethanethiol, 1, (151 mg, 0.2 mmole), potassium iodide (33 mg, 0.2 mmole), and potassium carbonate (280 mg, 2.0 mmole). The resulting slurry was then boiled overnight. Once the reaction was complete then the solution was allowed to cool to room temperature and then 2 g of silica gel was added and the solvent evaporated. The resulting solid was layered onto a silica gel column and eluted with one half percent ammonium hydroxide in 1:1 solution of ethyl acetate and hexanes. The title compound, 3, was recovered as a foam in 72- yield (141 mg). This was converted to the dihydrochloride; mp 166–168° C.; IR (KBr Disc) $cm^{-1}$ 1666; $^1H$ NMR ($CDCl_3$) 1.8–3.8, (m, 24H), 3.3 (s, 3H), 3.9–4.0 (m, 1H), 4.2–4.3 (m, 1H), 4.4–4.5 (m, 1H), 6.9–7.4 (m, 34 H), 8.7–8.9 (m, 1H), 9.3–9.4 (m, 1H). Calculated for $C_{62}H_{64}N_3O_3S_2F\cdot2$ HCl·2 $H_2O$: C, 68.24; H, 6.47; N, 3.85. Found: C, 38.03; H, 6.40; N, 3.82.

Route B

The amine nor-3β-(4-fluorophenyl)tropane-20-carboxylic acid methyl ester (52.6 mg, 0.2 mmole) was dissolved in dry methylene chloride (1 mL) and to this solution was added the 3-chloropropyltriflate (22.6 mg, 0.1 mmole, prepared from 3-chloropropanol). The resulting solution was stirred at room temperature for two hours at which point a further 10 mL of methylene chloride was added. The solution was filtered to remove excess amine triflate salt and filtrate evaporated and immediately dissolved in dry acetonitrile (10 mL). To this solution was added in succession N-{2-((2-(((triphenylmethyl)thio)ethyl)amino)acetyl}-S-(triphenylmethyl)-2-aminoethanethiol, 1, (136 mg, 0.2 mmole), potassium iodide (33 mg, 0.2 mmole), and potassium carbonate (280 mg, 2.0 mmole). The resulting slurry was then boiled overnight. Once the reaction was complete then the solution was allowed to cool to room temperature and then 2 g of silica gel was added and the solvent evaporated. The resulting solid was layered onto a silica gel column and eluted with one half percent ammonium hydroxide in 1:1 solution of ethyl acetate and hexanes. The title compound, 3, was recovered as a foam in 50% yield (98 mg) and was identical to that prepared by route A.

EXAMPLE 3

(RS)-N-{2-((3'-chloropropyl)(2-mercaptoethyl)-amino) acetyl)-2-aminoethanethiolato)rhenium (V) Oxide (Compound 4—FIG. 1)

N-{2-((3'-chloropropyl)(2-((triphenylmethyl)thio)ethyl) amino)acetyl}-S-(triphenylmethyl)-2-aminoethanethiol (2.5 g, 3.3 mmol) was dissolved in boiling ethanol (50 mL). To this was added a solution of tin (II) chloride (690 mg, in 6.25 mL of 0.05 M HCl), followed immediately by a solution of sodium perrhenate (1 g in 6.25 mL of 0.05 M HCl). Reflux was continued overnight, after which boiling acetonitrile (200 mL) was added and the resulting solution was filtered through a celite pad. The resultant cake was washed twice with boiling acetonitrile (2×200 mL). To the filtrate was added silica gel (30 g) and the solvent evaporated. The solid was then layered onto a silica gel column and eluted with ethyl acetate. The title compound was isolated pure in 480 yield (740 mg). Mp 218.4–218.8° C.; IR (KBr Disc) $cm^{-1}$ 1640, 952; $^1H$ NMR ($CDCl_3$) 1.67 (dt, 12 Hz, 4.6 Hz, 1H), 2.1–2.5 (m, 2H), 2.90 (dd, 13 Hz, 4.6 Hz, 1H), 3.1–3.5 (m, 4H), 3.64 (t, 6 Hz, 2H), 3.7–4.2 (m, 3H), 4.09 (d, 16 Hz, 1H), 4.5–4.7 (m, 1H), 4.68 (d, 16 Hz, 1H); HRCIMS calculated for $C_9H_{17}ClN_2S_2O_2Re$ $[MH]^+$ 470.9950, found 470.9971.

The corresponding $^{99m}Tc$ compound can be prepared by using sodium pertechnetate instead of sodium perrhenate.

EXAMPLE 4

(RS)-N-{2-((3'-N'-propyl-(1"R-3"β-(4-fluorophenyl) tropane-2"β-carboxylic acid methyl ester))(2-mercaptoethyl)amino)acetyl)-2-aminoethanethiolatojrhenium (V) Oxide. (Compound 5—FIG. 1). Compound O-861.

To a solution of 3β-(4-fluorophenyl)nortropane-20-carboxylic acid methyl ester (253 mg, 0.96 mmol) (Meltzer et al. *J. Med. Chem.* 1993, 36, 855) in dry acetonitrile (10 mL) was added in succession N-{2-((3'-chloropropyl)(2-mercaptoethyl)amino)acetyl)-2-aminoethanethiolato}rhenium (V) oxide (451 mg, 0.96 mmol), potassium iodide (159 mg, 0.96 mmol), and potassium carbonate (1.3 g, 9.6 mmol). The resulting slurry was then brought to reflux overnight. The solution was allowed to cool to room temperature and silica gel (10 g) was added and the solvent evaporated. The resultant solid was layered onto a silica gel column and eluted with 0.5% ammonium hydroxide in ethyl acetate. The title compound was recovered pure as a mixture of diastereomers in 90% yield (608 mg). Mp 101.9° C., IR (KBr Disc) $cm^{-1}$ 1720, 1666, 957; $^1H$ NMR ($CDCl_3$) 1.4–4.2, (m, 24H), 3.46 & 3.5 (2s, 3H), 4.4–4.7 (m, 1H), 4.80 & 4.82 (2d, 16 Hz, 1H), 6.8–7.3 (m, 4H); HRCIMS calculated for $C_{24}H_{34}FN_3S_2O_4Re$ $[MH]^+$ 698.1505, found 698.1557. This was converted to a hydrochloride for analysis: Calculated for $CH_{24}H_{33}FN_3O_4S_2Re\cdot HCl\cdot2$ $H_2O$: C, 37.47; H, 4.98; N, 5.46. Found C, 37.45; H, 4.95; N, 5.40.

EXAMPLE 5

(RS)-N-{2-((3'-N'-propyl-(1"R-3"β-(4-fluorophenyl) tropane-2"β-carboxylic acid methyl ester))(2-mercaptoethyl)amino)acetyl)-2-aminoethanethiolato}rhenium (V) Oxide. (Compound 5—FIG. 1). Compound O-861.

N-{2-((3'-N'-Propyl-3"β-(4-fluorophenyl)tropane-2"β-carboxylic acid methyl ester)(2-((triphenylmethyl)thio) ethyl)amino)acetyl}-S-(triphenylmethyl)-2-aminoethanethiol, 3, (98 mg, 0.1 mmole) was dissolved in boiling ethanol (1.5 mL). To this was added a solution of tin (II) chloride (21 mg, in 200 μL of 0.05 M HCl), followed immediately by a solution of sodium perrhenate (30 mg in 200 μL of 0.05 M HCl). Boiling was continued overnight, after which boiling acetonitrile (10 mL) was added and the resulting solution filtered through a pad of celite. The cake was further washed two more times with boiling acetonitrile (2×20 mL). To the filtrate was added silica gel (1 g) and the solvent evaporated. The solid was then layered onto a silica gel column and eluted with ethyl acetate. The title compound, 5, was isolated pure in 30% yield (21 mg) and was identical to that prepared by the route above.

The corresponding $^{99m}$Tc compound can be prepared by using sodium pertechnetate instead of sodium perrhenate.

The above reactions can be carried out with a variety of different nortropanes. Examples of additional compounds of the invention prepared in the same manner are given below in Examples 6–8.

EXAMPLE 6

(RS)-N(-2-((3'-N'-propyl-(1"R-3"β-(4-fluorophenyl) tropane-2"β-carboxylic acid methyl ester))(2-mercaptoethyl)amino)acetyl)-2-aminoethanethiolato}rhenium (V) Oxide. Compound O-862.

Mp 98.6–99.6° C., IR (KBr Disc) cm$^{-1}$ 1716, 1646, 957; $^1$H NMR (CDCl$_3$) 1.5–2.1 (m, 7H), 2.57 (t, 7 Hz, 2H), 2.8–4.0 (m, 13H), 3.52 (s, 3H), 4.0–4.3 (m, 2H), 4.5–4.7 (m, 1H), 4.75 & 4.74 (2d, 16 Hz, 1H), 6.85–7.30 (m, 4H); HRCIMS calculated for $C_{24}H_{34}N_3S_2O_4Re$ [MH-F]$^+$ 679.1521, found 679.1569. Calculated for $C_{24}H_{33}FN_3O_4S_2Re$•1.5 CHCl$_3$: C, 38.84; H, 4.59; N, 5.55. Found C, 38.91; H, 4.50; N, 5.44.

The corresponding $^{99m}$Tc compound can be prepared by using sodium pertechnetate instead of sodium perrhenate.

EXAMPLE 7

(RS)-N-2-((3'-N'-propyl-(1"R-3"β-(3,4-dichlorophenyl) tropane-2"β-carboxylic acid methyl ester))(2-mercaptoethyl) amino)acetyl)-2-aminoethanethiolato}rhenium (V) Oxide. Compound O-863.

Mp 108° C., IR (KBr Disc) cm$^{-1}$ 1724, 1653, 957; AH NMR (CDCl$_3$) 1.5–3.9 (m, 22H), 3.55 & 3.50 (2s, 3H), 3.9–4.2 (m, 2H), 4.5–4.7 (m, 1H), 4.80 (d, 16.4 Hz, 1H), 7.0–7.4 (m, 3H); HRCIMS calculated for $C_{24}H_{33}Cl_2N_3S_2O_4Re$ [MH]$^+$ 748.0819, found 748.0856. Calculated for $C_{24}H_{33}Cl_2N_3O_4S_2Re$: C, 38.55; H, 4.31; N, 5.62. Found C, 38.79; H, 4.38; N, 5.41.

The corresponding $^{99m}$Tc compound can be prepared by using sodium pertechnetate instead of sodium perrhenate.

EXAMPLE 8

(RS)-N-{2-((3'-N'-propyl-(1"S-3"α-((bis(4-fluorophenyl) methoxy)tropane-2"β-carboxylic acid methyl ester))(2-mercaptoethyl)amino)acetyl)-2-aminoethanethiolato}rhenium (V) Oxide. Compound O-864.

Mp 102° C., IR (KBr Disc) cm$^{-1}$ 1709, 1640, 957; $^1$H NMR (CDCl$_3$) 1.4–2.4 (m, 9H), 2.6–4.3 (m, 15H), 3.70 & 3.65 (2s, 3H), 4.4–4.7 (m, 1H), 4.85 & 4.69 (2d, 16 Hz, 1H), 5.35 (s, 1H), 6.8–7.4 (m, 8H); HRCIMS calculated for $C_{31}H_{39}F_2N_3S_2O_5Re$ [MH]$^+$ 822.1829, found 822.1818. Calculated for $C_{31}H_{38}F_2N_3O_5S_2Re$•2 H$_2$O: C, 43.45; H, 4.94; N, 4.90. Found C, 43.34; H, 4.68; N, 4.64.

The corresponding $^{99m}$Tc compound can be prepared by using sodium pertechnetate instead of sodium perrhenate.
Separation of Diastereomers OF O-864:

The diastereomeric mixture of O-864 was separated by silica gel column chromatography using 2% ammonia in ethyl acetate as the eluent. In this system diastereomer A eluted first and had an R$_f$ of 0.51 (100% ethyl acetate) and diastereomer B eluted second R$_f$ 0.43 (100% ethyl acetate)
Diastereomer A: Compound O-918. R$_f$ of 0.51 (100% ethyl acetate); $^1$H NMR (CDCl$_3$) 1.4–2.4 (m, 9H), 2.6–4.3 (m, 15H), 3.70 (s,3H), 4.4–4.7 (m, 1H) 4.85 (d, 16Hz, 1H), 5.35 (s,1H), 6.8–7.4 (m, 8H).
Diastereomer B: Compound O-919. R$_f$ 0.43 (100% ethyl acetate); $^1$H NMR (CDCl$_3$) 1.4–2.4 (m, 9H), 2.6–4.3 (m, 15H), 3.65 (s, 3H), 4.4–4.7 (m, 1H), 4.69 (d, 16 Hz, 1H), 5.35 (s, 1H), 6.8–7.4 (m, 8H).

EXAMPLE 9

(RS)-N-{2-((3'-N'-propyl-(1"R-3"β-(4-fluorophenyl) tropane-2"β-carboxylic acid methyl ester))(2-mercaptoethyl)amino)acetyl)-2-aminoethanethiolato}$^{99m}$technetium (V) Oxide (Compound 5—FIG. 1). Compound O-861T.

1.0–1.1 mg of the ligand N-{2-(3'-N'-propyl-(1"R-3"β-(4-fluorophenyl)tropane-2"β-carboxylic acid methyl ester)) ((2-((triphenylmethyl)thio)ethyl)amino)-acetyl}-S-(triphenylmethyl)-2-aminoethanethiol (Example 2) was dissolved in 0.3 mL anhydrous anisole and cooled in a icebath to 5° C., followed by 10 mL of anhydrous trifluoroacetic acid. A bright yellow colored solution resulted, which was stirred at 5° C. for 5 minutes. The reaction mixture was then titrated with triethylsilyl hydride until the color disappeared. The solution was then evaporated to dryness by rotary evaporation followed by high vacuum for 1 hour. The solid was then redissolved in 1.0 mL of distilled water previously deoxygenated and saturated with argon gas. 50–200 μL of this aqueous solution was added to 1.2–90 mCi of $^{99m}$Tc-glucoheptonate solution and incubated for 1 hour at 40° C.

Three μL of the resulting solution was analyzed by HPLC on a C$_8$ reverse phase column equipped with a C$_{18}$ guard column, eluted with 0.1 M ammonium acetate and acetonitrile under a linear gradient.

Figure 2:
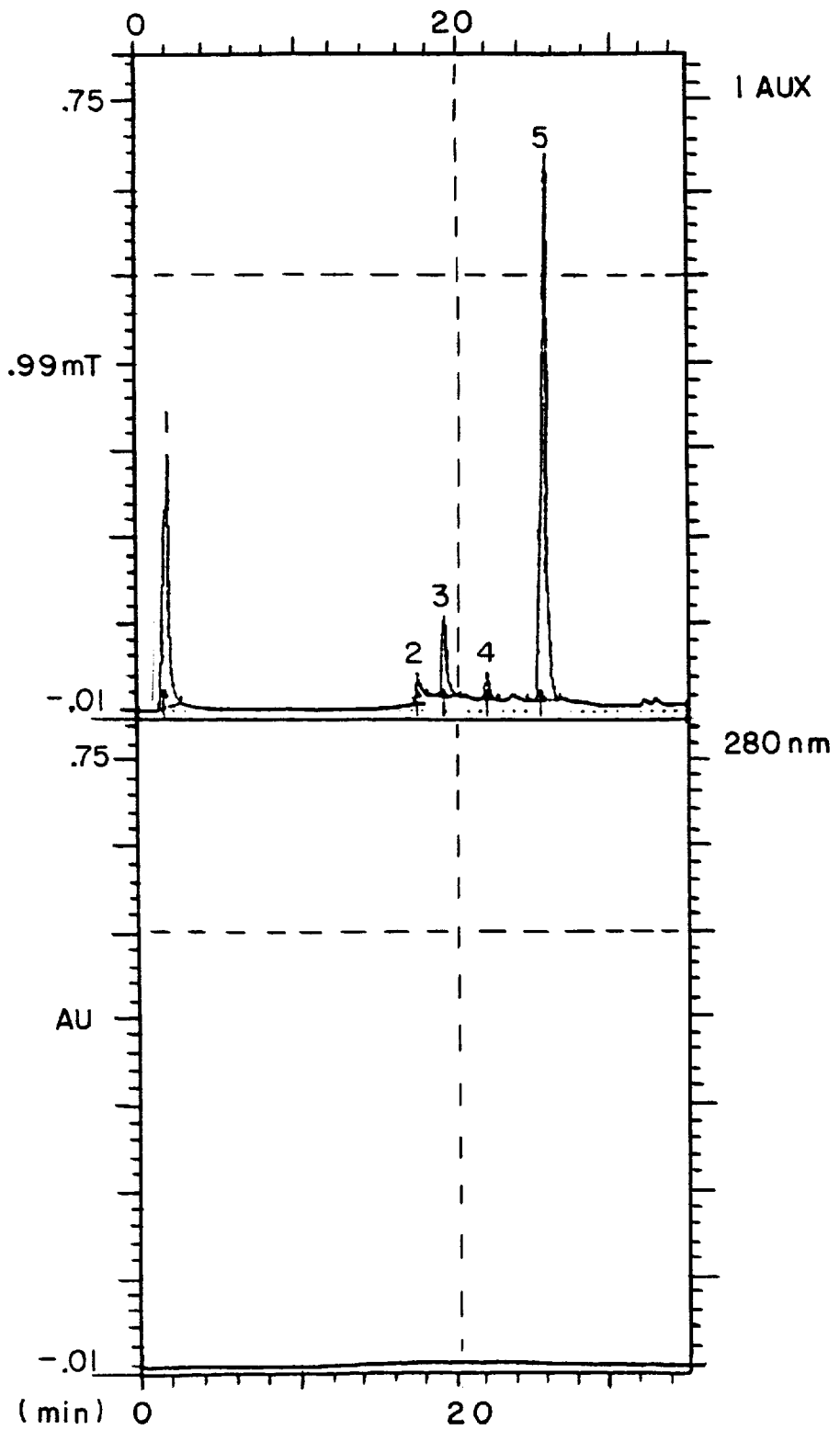
FIG. 2 is an HPLC profile showing (RS)-N-{2-((3'-N'-propyl-(1"R-3"β-(4-fluorophenyl)tropane-2"β-carboxylic acid methyl ester))(2-mercaptoethyl)amino)acetyl)-2-aminoethanethiolato}$^{99m}$technetium (V) Oxide at peak 5.

In the HPLC profile of FIG. 2, the top profile shows the radioactivity in the eluate. The desired $^{99m}$Tc labeled product has a retention time between 24–26 minutes, shown as peak 5. The bottom profile in FIG. 2 shows the UV active species in the eluate and demonstrates that the concentration of UV active species is below the detectable range. The fifth peak was collected in a round bottom flask and evaporated to minimum volume on a high volume rotary evaporator at room temperature. The product was subsequently reconstituted in 1 mL saline for injection. 350 μL (7.6 mCi) was used for injection into a rhesus monkey.

EXAMPLE 10

In Vitro Binding Assay

Binding of the labelled compounds of the present invention was tested as follows.

A. Tissue sources and preparation.

Brain tissue from adult male and female cynomolgus monkeys (Macaca fascicularis) was stored at −85° C. in the primate brain bank at the New England Regional Primate Research Center. The caudate-putamen was dissected from coronal slices and yielded 1.4±0.4 g tissue. Membranes were prepared as described previously (Madras et al., *J. Pharmacol. Exp. Ther.* 1989a, 251, 131–141). Briefly, the caudate-putamen was homogenized in 10 volumes (w/v) of ice-cold Tris.HCl buffer (50 mM, pH 7.4 at 4° C.) and centrifuged at 38,000× g for 20 min in the cold. The resulting pellet was suspended in 40 volumes of buffer, and the entire wash procedure was repeated twice. The membrane suspension (25 mg original wet weight of tissue/ml) was diluted to 12 mg/ml in buffer just before assay and was dispersed with a Brinkmann Polytron homogenizer (setting #5) for 15 sec. for assay with ($^3$H)WIN 35,428 to measure affinity at the DAT or ($^3$H)citalopram to measure affinity at the SET. All experiments were conducted in triplicate and each experiment was repeated in each of 2–3 preparations from individual brains.

B. Dopamine transporter assay.

The dopamine transporter was labeled with ($^3$H)WIN 35,428 (($^3$H)CFT, 2β-carbomethoxy-3β-(4-fluorophenyl)-N-($^3$H)methyltropane, 81.04 Ci/mmol, DuPont-NEN). The affinity of ($^3$H)CFT for the dopamine transporter was determined in experiments by incubating tissue with a fixed concentration of ($^3$H)CFT and a range of concentrations of unlabeled CFT. The assay tubes received, in Tris.HCl buffer (50 mM, pH 7.4 at 0–4° C.; NaCl 100 mM), the following constituents at a final assay concentration: CFT, 0.2 ml (1 pM–100 nM), ($^3$H)CFT (0.3 nM); membrane preparation 0.2 ml (4 mg original wet weight of tissue/ml). The 2 h incubation (0–4° C.) was initiated by addition of membranes and terminated by rapid filtration over Whatman GF/B glass fiber filters pre-soaked in 0.1% bovine serum albumin (Sigma Chem. Co.). The filters were washed twice with 5 ml Tris.HCl buffer (50 mM), incubated overnight at 0–4° C. in scintillation fluor (Beckman Ready-Value, 5 ml) and radioactivity was measured by liquid scintillation spectrometry (Beckman 1801). Cpm were converted to dpm following determination of counting efficiency (>45%) of each vial by external standardization. Total binding was defined as ($^3$H) CFT bound in the presence of ineffective concentrations of unlabeled CFT (1 or 10 pM). Non-specific binding was defined as ($^3$H)CFT bound in the presence of an excess (30 μM) of (−)-cocaine. Specific binding was the difference between the two values.

Competition experiments to determine the affinities of the novel compounds at ($^3$H)CFT binding sites were conducted using procedures similar to those outlined above with the novel drug substituted for the unlabeled CFT. Stock solutions of the water-soluble compounds were dissolved in doubly distilled water or buffer and stock solutions of other drugs were made in a range of ethanol/HCl solutions. Several of the drugs were sonicated to promote solubility. The stock solutions were diluted serially in the assay buffer and added (0.2 ml) to the assay medium as described above.

C. Serotonin transporter assay.

The serotonin transporter was assayed in caudate-putamen membranes using conditions similar to those for the dopamine transporter. The affinity of ($^3$H)citalopram (specific activity: 81.86 Ci/mmol, DuPont-NEN) for the serotonin transporter was determined in experiments by incubating tissue with a fixed concentration of ($^3$H) citalopram and a range of concentrations of unlabeled citalopram. The assay tubes received, in Tris.HCl buffer (50 mM, pH 7.4 at 0–4° C.; NaCl 100 mM), the following constituents at a final assay concentration: citalopram, 0.2 ml (1 pM–100 nM), ($^3$H)citalopram (1 nM); membrane preparation 0.2 ml (4 mg original wet weight of tissue/ml). The 2 h incubation (0–4° C.) was initiated by addition of membranes and terminated by rapid filtration over Whatman GF/B glass fiber filters pre-soaked in 0.1% polyethyleneimine. The filters were washed twice with 5 ml Tris.HCl buffer (50 mM), incubated overnight at 0–4° C. in scintillation fluor (Beckman Ready-Value, 5 ml) and radioactivity was measured by liquid scintillation spectrometry (Beckman 1801). Cpm were converted to dpm following determination of counting efficiency (>45%) of each vial by external standardization. Total binding was defined as ($^3$H) citalopram bound in the presence of ineffective concentrations of unlabeled citalopram (1 or 10 pM). Non-specific binding was defined as ($^3$H)citalopram bound in the presence of an excess (10 μM) of fluoxetine. Specific binding was the difference between the two values.

Competition experiments to determine the affinities of other drugs at ($^3$H)citalopram binding sites were conducted using procedures similar to those outlined above.

A Beckman 1801 Scintillation Counter was used for scintillation spectrometry.

D. Data analysis.

Data were analyzed by the EBDA and LIGAND computer software programs (Elsevier-Biosoft, U.K.). Final estimates of $IC_{50}$ and nH values were computed by the EBDA program. Baseline values for the individual drugs were established by computer analysis, using the baseline drugs as a guide. The LIGAND program provided final parameter estimates for the affinity of the radioligand ($K_d$) by iterative non-linear curve-fitting.

TABLE 1

Affinity of compounds at the dopamine transporter (DA; dihydroxyphenethylamine) and the serotonin transporter (5HT; 5-hydroxytryptamine).

| COMPOUND | DA Transporter $IC_{50}$ (nM) | 5HT Transporter $IC_{50}$ (nM) | DA/5HT Selectivity Ratio |
|---|---|---|---|
| O-861 | 5.99 ± 0.81 | 124 ± 17 | 21 |
| O-862 | 2963 ± 157 | 5021 ± 1882 | 1.7 |
| O-863 | 37.2 ± 3.4 | 264 ± 16 | 7.1 |
| O-864 | 616 ± 88 | 55,200 ± 20,000 | 90 |

O-861 (see Examples 4 and 5) bound to the dopamine transporter with twice the affinity ($IC_{50}$: 5.99±0.81 nM (n=7)) of WIN 35,428, measured under the same conditions. Predictably, the 2β-isomer, O-861 was 500 times more potent than the 2α-isomer, O-862 (see Example 6). O-861 was 6 times more potent than O-863 (see Example 7), the dichloro analog of O-861, and 103 times more potent than O-864 (see Example 8), the corresponding 2-carbomethoxy benztropine derivative. Each of the compounds were labeled with rhenium for these in vitro assays.

Based on $IC_{50}$ values, O-861 was 21-fold more selective for the dopamine over the serotonin transporter. Thus O-861 was more potent and selective than WIN 35,428 for the dopamine transporter.

EXAMPLE 11
IN VIVO BINDING Of Compound O-861 TO THE DOPAMINE TRANSPORTER IN BRAIN A. Positron Emission Tomography (PET) imaging methods.

PET imaging was conducted in three cynomolgus monkeys (Macaca fascicularis, 2–3 kg) in order to assess whether O-861 penetrated the blood-brain barrier and occupied the dopamine transporter. The dopamine transporter was labeled with ($^{11}$C)WIN 35,428. Animals were anesthetized, placed in a headholder, and their brains were imaged with a PET camera with a 4.5 mm resolution. The curves were derived using a nonlinear least squares fitting program (MatLab, not shown). The ratio of specific to non-specific binding was determined by comparing the uptake in the caudate and putamen with that of the cerebellum. One monkey served as a control for the study. A second animal was pre-treated with O-861 (1 mg/kg) 30 minutes prior to the time the PET imaging ligand was injected. Data was collected for as long as 90 minutes. A third animal was treated with O-861 (1 mg/kg) 20 minutes after the start of the PET imaging procedure. The data shown below indicate that pretreatment with O-861 resulted in a reduction in the ($^{11}$C)WIN 35,428 accumulation in caudate and putamen. These results suggest that O-861 enters the brain and blocks the binding of ($^{11}$C)WIN 35,428 to the dopamine transporter.

These results demonstrate that O-861 displays high affinity and relatively high dopamine over serotonin transporter selectivity. Its binding properties are superior to that of the highly effective PET imaging agent and parent compound WIN 35,428. Data also show that O-861 striatum:cerebellum ratios were decreased in an animal pretreated with the drug, compared with a control animal.

TABLE 2

($^{11}$C) WIN 35,428 Accumulation In The Caudate and Putamen

| TREATMENT | 40 min | 60 min | 90 min |
|---|---|---|---|
| CONTROL | | | |
| Putamen: cerebellum | 2.33 | 2.97 | 4.22 |
| Caudate: cerebellum | 2.02 | 2.50 | 3.57 |
| PRE-TREATMENT | | | |
| Putamen: cerebellum | 1.94 | 2.34 | 3.17 |
|  | (−16%) | (−20%) | (−25%) |
| Caudate: cerebellum | 1.56 | 1.94 | 2.25 |
|  | (−23%) | (−22%) | (−37%) |
| POST-TREATMENT | | | |
| Putamen: cerebellum | 2.26 | 2.82 | 3.51 |
|  | (−3%) | (−3%) | (−17%) |
| Caudate: cerebellum | 1.95 | 2.35 | 2.92 |
|  | (−4%) | (−6%) | (−18%) |

The present invention has been described in detail, including the preferred embodiments thereof. However, it will be appreciated that those skilled in the art, upon consideration of the present disclosure, may make modifications and/or improvements of this invention and still be within the scope and spirit of this invention as set forth in the following claims.

We claim:

1. A radiopharmaceutical compound which is capable of complexing with $^{99m}$Tc, said compound having the following structural formula:

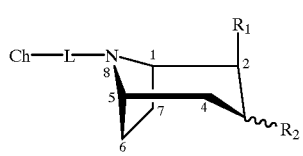

(I)

wherein
R$_1$ is selected from COOR$^a$, COR$^a$, CONHR$^a$, CONR$^a$R$^b$, CH$_2$CH$_3$, (CH$_2$)$_n$CH$_3$, CHCHR$^c$, (CH$_2$)$_n$CCR$^c$ or an ester bioisostere;
R$_2$ is selected from C$_6$H$_4$X, C$_6$H$_3$X$_2$, C$_{10}$H$_6$X, or C$_{12}$H$_8$WYCHO (diarylmethoxy);
R$^a$ and R$^b$ are each selected from CH$_3$, CH$_2$CH$_3$, CH$_2$CH$_2$CH$_3$, (CH$_2$)$_n$CH$_3$, CH(CH$_3$)$_2$, C(CH$_3$)$_3$, (CH$_2$)$_n$C$_6$H$_5$, C$_6$H$_5$, C$_6$H$_4$X, C$_{10}$H$_7$, or C$_{10}$H$_6$X;
R$^c$ is selected from COOR$^a$, CH$_3$, (CH$_2$)$_n$CH$_3$, C$_6$H$_5$, C$_6$H$_4$X, C$_{10}$H$_7$, or C$_{10}$H$_6$X;
X is selected from H, Br, Cl, I, F, OH, OCH$_3$, CF$_3$, NO$_2$, NH$_2$, CN, OR, NHCOCH$_3$, N(CH$_3$)$_2$, CH$_2$CH$_3$, CHOCH$_3$, C(CH$_3$)$_3$;

W and Y are each selected from H, Br, Cl, I, F, OH, OCH$_3$, CF$_3$, NO$_2$, NH$_2$, CN, OR, NHCOCH$_3$, N(CH$_3$)$_2$;
n is an integer 0–6;
L is a linking moiety comprising a chain of atoms containing 2 to about 6 carbon atoms in the backbone of the chain or, if a ring is part of the chain, 1 to about 4 carbon atoms in the backbone of the chain in addition to the ring carbons; and
Ch is a tridentate or tetradentate chelating ligand capable of forming a neutral complex with technetium or rhenium.

2. The compound according to claim 1 labeled with a radionuclide that is complexed with the chelating ligand.

3. The compound according to claim 1, wherein the radionuclide is $^{99m}$Tc.

4. The compound according to claim 1, wherein the radionuclide is rhenium.

5. The compound according to claim 1, wherein the ester bioisostere is C$_3$HNOR$^c$ or C$_2$N$_2$OR$^c$.

6. The compound according to claim 1, wherein the linking moiety is selected from the group consisting of (CH$_2$)$_m$, CH$_2$(CH$_2$)$_m$CH$_2$, (CH$_2$)$_m$C$_6$H$_4$(CH$_2$)$_p$, CH$_2$(CHCH) CH$_2$, CH$_2$CCCH$_2$, (CH$_2$)$_m$NHR(CH$_2$), (CH$_2$)$_m$O (CH$_2$), (CH$_2$)$_m$S(CH$_2$), CH$_2$CONH (CH$_2$)$_m$, (CH$_2$)$_m$CONH (CH$_2$)$_p$, and (CH$_2$)$_m$COO(CH$_2$)$_p$, where m=0–5, p=0–5, and (m+p)=1–5, the linking moiety having a backbone chain length of 2 to about 6 carbon atoms, wherein a benzene ring in the backbone is equivalent to about 2 carbon atoms in chain length.

7. The coordination compound according to claim 1, wherein the chelating ligand comprises a bisamido-bisthiol or a monoamide,monoamino-bisthiol group covalently attached to linker L wherein the bisamido-bisthiol or monoamide, monoamino-bisthiol group has the following structural formula:

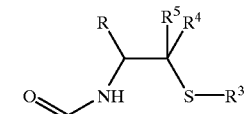

(III)

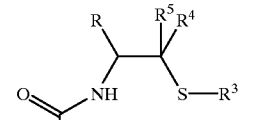

and

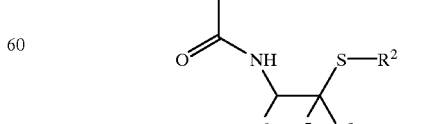

(IV)

and

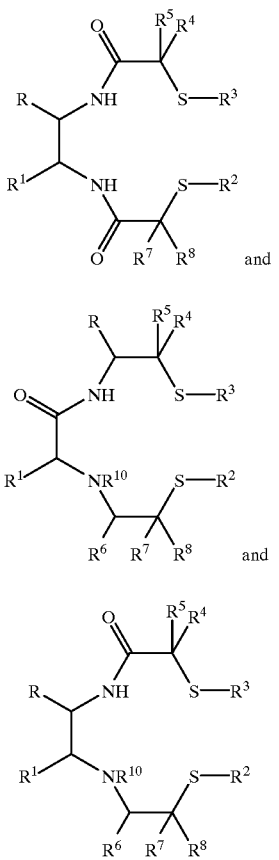

wherein R, R⁶, and R¹⁰ are each selected from hydrogen, substituted or unsubstituted lower alkyl, alkylR⁹, or —COR⁹ where R⁹ is selected from hydroxy, substituted lower alkoxy, substituted or unsubstituted amino, glycine ester, chloro, bromo, iodo, or OR, wherein OR is a leaving group selected from mesylate, triflate, or tosylate or an activated leaving group; R¹ is selected from hydrogen, or substituted or unsubstituted lower alkyl; R² and R³ are each selected from hydrogen or a thiol protecting group or an inter or intramolecular disulfide; and R⁴, R⁵, R⁷ and R⁸ are each selected from hydrogen or lower alkyl.

8. The compound according to claim 1, wherein the chelating ligand is a monoaminomonoamide.

9. The compound according to claim 1, wherein the chelating ligand is N-(2-((2-((triphenylmethyl)thio)-ethyl)amino)acetyl)-S-(triphenylmethyl)-2-aminoethanethiol.

10. The compound according to claim 1, wherein the tropane ligand is selected from 2-carbomethoxy-3-(4-fluorophenyl)-N-methyltropane, 2-carbomethoxy-3-(3,4-dichlorophenyl)-N-methyltropane and (S)-(+)-2-carbomethoxy-3α-(bis(4-fluorophenyl)methoxy)tropane.

11. N-2-((3¹-N'-propyl-(1"R-3"β-(4-fluorophenyl)tropane-2"β-carboxylic acid methyl ester))((2-((triphenylmethyl)thio)-ethyl)amino)acetyl)-S-(triphenylmethyl)-2-aminoethanethiol.

12. N-2-((3'-N'-propyl-(1"R-3"β-(3,4-dichlorophenyl)tropane-2"β-carboxylic acid methyl ester))((2-((triphenylmethyl)thio)ethyl)amino)acetyl)-S-(triphenylmethyl)-2-aminoethanethiol.

13. N-2-((3'-N'-propyl-(1"S-3"α-((bis(4-fluorophenyl)methoxyl)tropane-2"β-carboxylic acid methyl ester))((2-((triphenylmethyl)thio)ethyl)amino)acetyl)-S-(triphenylmethyl)-2-aminoethanethiol.

14. (RS)-N-{2-((3'-N'-propyl-(1"R-3"β-(4-fluorophenyl)tropane-2"β-carboxylic acid methyl ester))(2-mercaptoethyl)amino)-acetyl)-2-aminoethanethiolato}⁹⁹ᵐtechnetium (V) Oxide.

15. (RS)-N-{2-((3'-N'-propyl-(1"R-3"β-(4-fluorophenyl)tropane-2"β-carboxylic acid methyl ester))(2-mercaptoethyl)amino)-acetyl)-2-aminoethanethiolato}rhenium (V) Oxide.

16. (RS)-N-2-((3'-N'-propyl-(1"R-3"β-(4-fluorophenyl)tropane-2"α-carboxylic acid methyl ester))(2-mercaptoethyl)amino)-acetyl)-2-aminoethanethiol.

17. (RS)-N-{2-((3'-N'-propyl-(1"R-3"β-(4-fluorophenyl)-tropane-2"α-carboxylic acid methyl ester))(2-mercaptoethyl) amino)acetyl)-2-aminoethanethiolato}⁹⁹ᵐtechnetium (V) Oxide.

18. (RS)-N-{2-((3'-N'-propyl-(1"R-3"β-(4-fluorophenyl)-tropane-2"α-carboxylic acid methyl ester))(2-mercaptoethyl) amino)acetyl)-2-aminoethanethiolato}rhenium (V) Oxide.

19. (RS)-N-2-((3'-N'-propyl-(1"R-3"β-(3,4-dichlorophenyl)-tropane-2"β-carboxylic acid methyl ester))(2-mercaptoethyl) amino)acetyl)-2-aminoethanethiol.

20. (RS)-N-{2-((3'-N'-propyl-(1"R-3"β-(3,4-dichlorophenyl)-tropane-2"β-carboxylic acid methyl ester))(2-mercaptoethyl) amino)acetyl)-2-aminoethanethiolato}⁹⁹ᵐtechnetium (V) Oxide.

21. (RS)-N-{2-((3'-N'-propyl-(1"R-3"β-(3,4-dichlorophenyl)-tropane-2"β-carboxylic acid methyl ester))(2-mercaptoethyl) amino)acetyl)-2-aminoethanethiolato}rhenium (V) Oxide.

22. (RS)-N-2-((3'-N'-propyl-(1"S-3"α-((bis(4-fluorophenyl)methoxy)tropane-2"β-carboxylic acid methyl ester))(2-mercaptoethyl)amino)acetyl)-2-aminoethanethiol.

23. (RS)-N-{2-((3'-N'-propyl-(1"S-3"α-((bis(4-fluorophenyl)methoxy)tropane-2"β-carboxylic acid methyl ester))(2-mercaptoethyl)amino)acetyl)-2-aminoethanethiolato}⁹⁹ᵐtechnetium (V) Oxide.

24. (RS)-N-{2-((3'-N'-propyl-(1"S-3"α-((bis(4-fluorophenyl)methoxy)tropane-2"β-carboxylic acid methyl ester))(2-mercaptoethyl)amino)acetyl)-2-aminoethanethiolato}rhenium (V) Oxide.

25. A radiopharmaceutical compound selected from the group consisting of (R)-N-{2-((3'-N'-propyl-(1"R-3"β-(4-fluorophenyl)tropane-2"β-carboxylic acid methyl ester))(2-mercaptoethyl)amino)-acetyl)-2-aminoethanethiolato}⁹⁹mtechnetium (V) Oxide, (R)-N-{2-((3'-N'-propyl-(1"R-3"-(4-fluorophenyl)-tropane- 2"α-carboxylic acid methyl ester))(2-mercaptoethyl) amino) acetyl)-2-aminoethanethiolato}⁹⁹ᵐtechnetium (V) Oxide, (R)-N-{2-((3'-N'-propyl-(1"R-3"β-(3,4-dichlorophenyl)-tropane-2"β-carboxylic acid methyl ester))(2-mercaptoethyl) amino)acetyl)-2-aminoethanethiolato}⁹⁹ᵐtechnetium (V) Oxide, and (R)-N-{2-((3'-N'-propyl-(1"S-3"α-((bis(4-fluorophenyl)methoxy)tropane-2"β-carboxylic acid methyl ester))(2-mercaptoethyl)amino)acetyl)-2-aminoethanethiolato}⁹⁹ᵐtechnetium (V) Oxide.

26. A radiopharmaceutical compound selected from the group consisting of (S)-N-{2-((3'-N'-propyl-(1"R-3"β-(4-fluorophenyl)tropane-2"β-carboxylic acid methyl ester))(2-mercaptoethyl)amino)-acetyl)-2-aminoethanethiolato}⁹⁹ᵐtechnetium (V) Oxide, (S)-N-{2-((3'-N'-propyl-(1"R-3"β-(4-fluorophenyl)-tropane-2"α-carboxylic acid methyl ester))(2-mercaptoethyl) amino) acetyl)-2-aminoethanethiolato}⁹⁹ᵐtechnetium (V) Oxide, (S)-N-{2-((3'-N'-propyl-(1"R-3"β-(3,4-dichlorophenyl)-tropane-2"β-carboxylic acid methyl ester))(2- mercaptoethyl) amino)acetyl)-2-aminoethanethiolato}$^{99m}$technetium (V) Oxide, and (S)-N-{2-((3'-N'-propyl-(1"S-3"α-((bis(4-fluorophenyl)methoxy)tropane-2"β-carboxylic acid methyl ester))(2-mercaptoethyl)amino)acetyl)-2-aminoethanethiolato}$^{99m}$technetium (V) Oxide.

27. A method for detecting the density of tropane recognition sites in a mammal as an indication of neurodegenerative or neuropsychiatric disorders characterized by changes in the density of dopamine transporters or dopamine neurons, said method comprising providing in a suitable pharmacological carrier a radiopharmaceutical compound according to claim 1 labeled with $^{99m}$Tc, injecting the compound into the mammal and scanning the mammal using a radiodiagnostic imaging apparatus.

28. A method for monitoring in a mammal neurodegenerative or neuropsychiatric disorders characterized by changes in the density of dopamine transporters or dopamine neurons, said method comprising providing in a suitable pharmacological carrier a radiopharmaceutical compound according to claim 1 labeled with $^{99m}$Tc, injecting the compound into the mammal and scanning the mammal using a radiodiagnostic imaging apparatus.

29. A radiopharmaceutical kit for preparing a radiopharmaceutical preparation, said kit comprising a sealed, sterile, apyrogenic vial containing a radiopharmaceutical compound of claim 1 and a reducing agent for labeling said compound with a radionuclide.

30. The radiopharmaceutical kit according to claim 25 wherein the reducing agent is a stannous compound.

* * * * *

UNITED STATES PATENT AND TRADEMARK OFFICE
CERTIFICATE OF CORRECTION

PATENT NO.     : 6,171,576 B1
DATED          : January 9, 2001
INVENTOR(S)    : Meltzer et al.

It is certified that error appears in the above-identified patent and that said Letters Patent is hereby corrected as shown below:

Column 24,
Line 13, replace "according to claim 25" with -- according to claim 29 --.

Signed and Sealed this

Eighth Day of October, 2002

*Attest:*

*Attesting Officer*

JAMES E. ROGAN
*Director of the United States Patent and Trademark Office*